United States Patent [19]

Venturi et al.

[11] Patent Number: 4,862,882

[45] Date of Patent: Sep. 5, 1989

[54] APPARATUS FOR THE PERFORATION OF THE FEMUR AND THE TIBIA IN SURGICAL OPERATIONS

[75] Inventors: Giancarlo Venturi, Pianoro; Carlo Bedogni, Rimini; Bruno Fregni, Pianoro, all of Italy

[73] Assignee: Italpres S.n.c. di Fregni Bruno & C., Pianoro BO, Italy

[21] Appl. No.: 220,651

[22] Filed: Jul. 18, 1988

[30] Foreign Application Priority Data

Jul. 20, 1987 [IT] Italy ................................ 3563 A/87

[51] Int. Cl.[4] .......................................... A61B 17/56
[52] U.S. Cl. ........................... 128/92 VD; 128/92 VL; 128/92 V
[58] Field of Search ............... 128/92 R, 92 YJ, 92 V, 128/92 VY, 92 VW, 92 VV, 92 VD, 92 VL; 623/13

[56] References Cited

U.S. PATENT DOCUMENTS

| | | | |
|---|---|---|---|
| 4,257,411 | 3/1981 | Cho ................................ | 128/92 VD |
| 4,722,331 | 2/1988 | Fox ................................ | 128/92 VD |
| 4,739,751 | 4/1988 | Sapega et al. ................... | 128/92 VD |
| 4,781,182 | 11/1988 | Purnell et al. .................. | 128/92 VD |

FOREIGN PATENT DOCUMENTS

2747568   4/1979   Fed. Rep. of Germany ... 128/92 V

Primary Examiner—Robert A. Hafer
Assistant Examiner—Kevin G. Rooney
Attorney, Agent, or Firm—Guido Modiano; Albert Josif

[57] ABSTRACT

The apparatus is designed for the installation of front and rear crossed prosthetic ligaments in the articulation of the knee, and includes a stem which extends, at one end, with an arc-like tapered portion the end whereof is adapted to be inserted through the surgical opening at the knee, to pass between the tibial plate and the condyloid cavity and to be positioned in the exact outlet position of the bore to be provided, a small block having at least one hole for a screw for fastening to the bone and a seat for coupling to a spherical joint, an arm which ends at one end with the spherical joint coupled to the seat, bears at the other end a clamp with a groove and counter groove for its longitudinal sliding and locking along the stem and has coupling elements for interchangeable bushes for guiding the drilling tool.

7 Claims, 2 Drawing Sheets

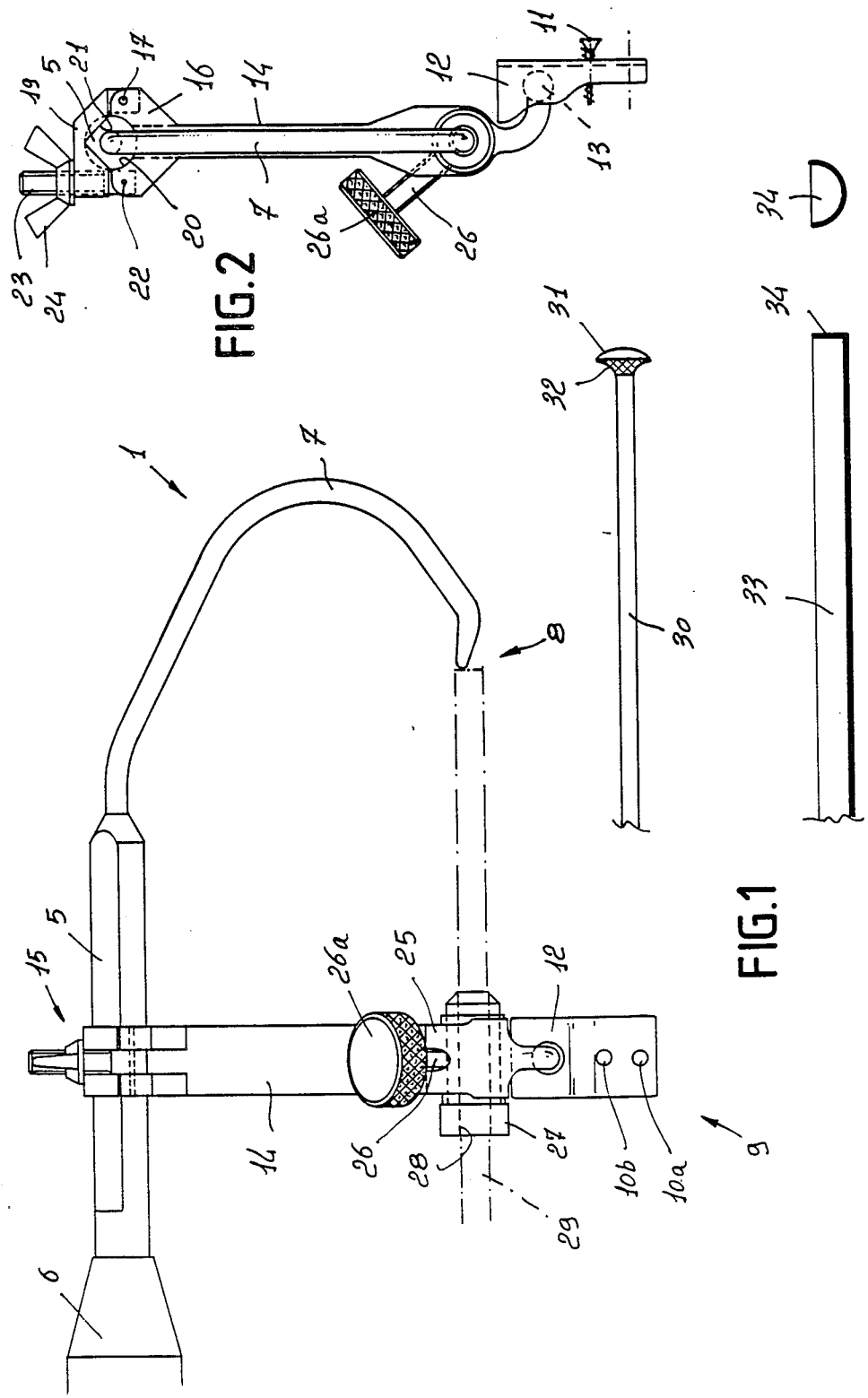

APPARATUS FOR THE PERFORATION OF THE FEMUR AND THE TIBIA IN SURGICAL OPERATIONS

BACKGROUND OF THE INVENTION

The present invention relates to an apparatus for the perforation of the femur and the tibia in surgical operations, particularly for installing front and rear crossed prosthetic ligaments in the articulation of the knee.

In a recent implantological method the ligaments of the knee can be replaced with bands or strands of particular biocompatible materials: such bands are inserted in two corresponding bores which must have their inlets substantially on the front faces of the tibia and of the femur and their outlets in the rear regions respectively of the tibial plate and of the condyloid cavity of the femur. The ends of the bands, conveniently provided with slots or the like, are connected at the bores inlets by screws which are intended to be definitely removed, after the fibers have biologically associated with the bone.

It has been observed that a long time is required by this surgery for the installation of the prosthetic ligaments because of the difficulties encountered in providing the bores in the bones. For a good operation of the knee joint, in fact, bore outlets must be located in extremely precise positions (surgical points), defined by the surgeon, which, however, are located behind the knee on the opposite side with respect to that on which the patient is operated.

Currently, a first small test bore is drilled using a small bit with great care and caution, checking the alignment as the bit drills through the bone; the surgeon then manually checks the location of the bore outlet by passing a finger behind the articulation; if the bore outlet is considered to be acceptably located, the bore is progressively widened with increasingly larger-diameter bits with the aid of steel guide wires inserted in the bore; if instead the bore outlet is in a position which is considered unacceptable, another bore is drilled.

It is obvious that, also in view of the fact that the bore is inclined with respect to the surface of the bone, there are great difficulties in drilling the bores correctly.

Another great difficulty is due to the fact that in the bore outlet regions there are vessels and tissues which must absolutely not be damaged by the drill bit: finally the bore outlets must be bevelled to avoid stresses which may damage the fibers of the band.

SUMMARY OF THE INVENTION

The aim of the present invention is to eliminate the abovementioned disadvantages and to provide an apparatus which allows to perform the perforation of the femur and the tibia in an extremely fast and precise manner with the assurance of not damaging the underlying tissues so as to make the surgical operation much more rapid and less traumatic.

Within this aim, an object of the present invention is to achieve the above described aim with a simple structure which is relatively easy to manufacture, is safe and effective in use and has a relatively modest cost.

This aim and these objects are achieved by an apparatus for the perforation of the femur and the tibia in surgical operations, particularly for installing the front and rear crossed prosthetic ligaments in the articulation of the knee, characterized in that it comprises: a stem having an arc-like tapered portion, one end of said arc-like portion being adapted to be inserted in the surgical opening at the knee and pass between the tibial plate and the condyloid cavity and to be positioned in the exact outlet position of a bore to be drilled, a small block having at least one hole for a screw for fastening it to the bone, said block having a seat for engaging a spherical joint, an arm having said spherical joint at one end, said arm bearing a clamp at its end opposite said spherical joint, said clamp having a guide means, said clamp being slideable and lockable along said stem and having coupling means for interchangeable bushes for guiding a drilling tool.

BRIEF DESCRIPTION OF THE DRAWINGS

Further characteristics and advantages of the invention will become apparent from the detailed description of a preferred but not exclusive embodiment of an apparatus according to the invention, illustrated only by way of non-limitative example in the accompanying drawings, wherein:

FIG. 1 is a lateral view of the apparatus according to the invention;

FIG. 2 is a front view of the apparatus of FIG. 1;

DESCRIPTION OF THE PREFERRED EMBODIMENTS

Figure 3:
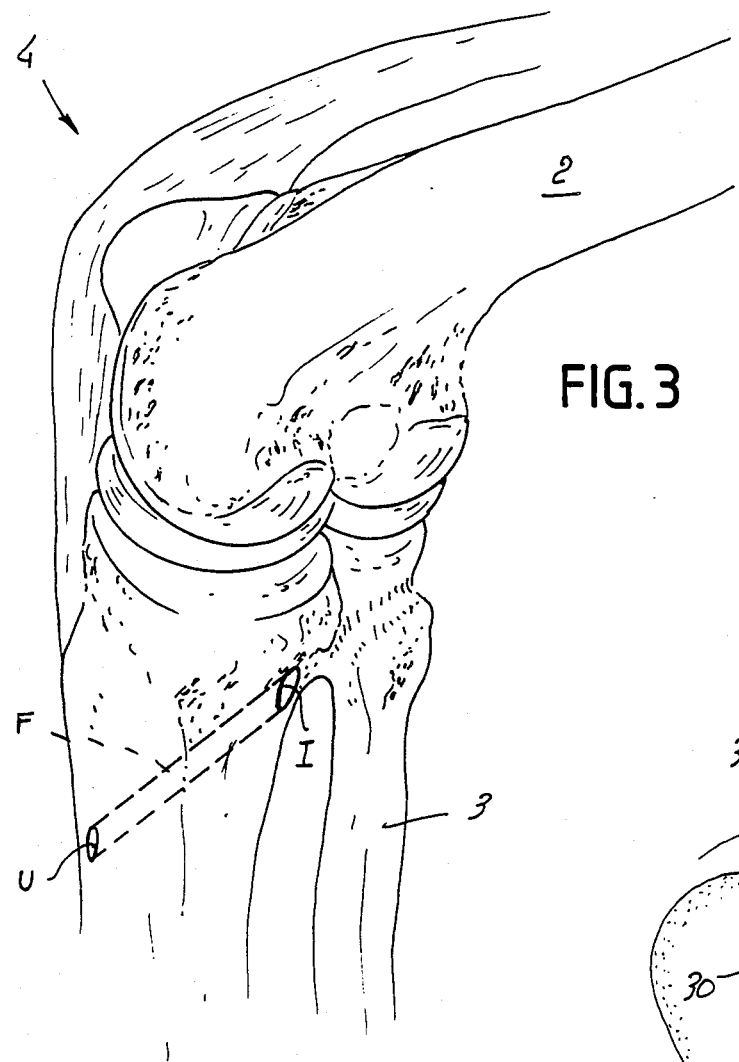
FIGS. 3 and 4 are schematic views of the apparatus applied to the bone in two successive operating steps.
Figure 4:
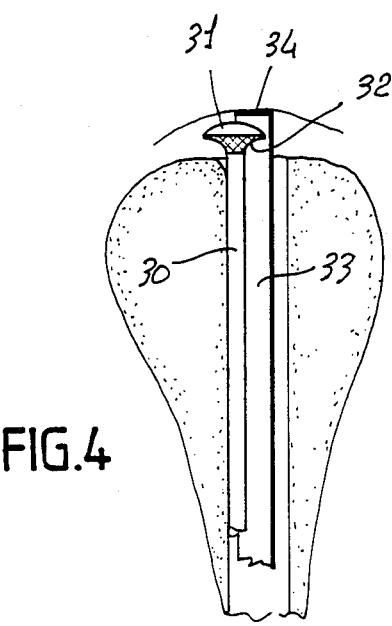

With reference to the figures, reference numeral 1 generally indicates the apparatus according to the invention for the perforation of femur 2 and of tibia 3 for installing the front and rear crossed prosthetic ligaments in the articulation of the knee 4.

The apparatus 1 comprises a preferably rectilinear prismatic stem 5 having a hexagonal cross section and a handgrip 6 at one end. At the opposite side of the handgrip, the stem 5 extends in an arc-like tapered portion 7 which has a mixed-line configuration and ends with a rounded tip 8. According to a different aspect of the invention the stem 5 has a cross section half circular and half square-cornered, as illustrated in the figures.

Reference numeral 9 indicates a small block which has at least one hole 10 (in the illustrated embodiment there are two holes 10a and 10b), for fastening the block to the bone with a screw 11, and has a seat 12 for its connection to a spherical joint 13.

An arm 14 has a joint 13 at one end and a clamp 15 at the other end. The clamp 15 has a jaw 16 rigidly associated with the arm 14. A jaw 19 is articulated to said jaw 16 by means of a dowel 17. The jaws 16 and 19 respectively have a groove 20 and a countergroove 21, which match the outer cross section of the prismatic stem 5.

On the opposite side with respect to the dowel 17, the jaw 16 defines a fork at which the terminal eyelet of a threaded stem 23 is articulated by means of a pivot 22; the jaw 19 has, in turn, its end in the shape of a fork in which the threaded stem 23 is insertable and is engaged by a wing nut 24: by tightening the wing nut 24 it is possible to rigidly couple the arm 14 in any position along the stem 5 and prevent its relative rotation.

The arm 14 can thus be locked in any position substantially on the plane defined by the stem 5 and by the mixed-line portion 7. In the arm 14, at a distance from the stem 5 which is equal to the distance of the stem from the tip 8, a counterbush 25 is provided which has an axis parallel to the stem 5 and is directed towards the tip 8. A screw 26, having an actuation knob 26a, is screwable to an inclined threaded hole provided in the counterbush 25 and constitute a coupling means for an interchangeable bush 27 which is internally traversed by a guide hole 28 for the bit 29 which is adapted to drill the bore in the bone: the bushes are progressively replaced with others having a larger-diameter hole for progressively larger bits.

The operation of the apparatus according to the invention is as follows: through a surgical entry point executed in front of the tibia or of the femur, the tip 8 is introduced between the tibial plate and the condyloid cavity until said tip is in the exact surgical point in which the bore to be drilled must have its outlet; the small block 9 is fixed to the femur or to the tibia by means of at least one screw 11. The arm 14 is rotated about the small block 9 and the clamp 15 is slipped along the stem 5 and subsequently locked by means of nut 24 so as to move the tip 8 into the exact outlet position U of the bore F which is to be drilled and the counterbush 25 into alignment with the bore inlet I. Once the smallest-diameter bush 27 is mounted, a first small bore with a reduced diameter is drilled with the bit 29 and subsequently, by changing the bush and the bit, the bore is widened until it reaches the required diameter.

The block 9 and thus the entire apparatus are now removed, and the outlet U is bevelled by means of a mushroom-shaped bit constituted by a tool stem 30 which is coupled to a drill and ends with a mushroom-shaped head 31 having its abrasive part 32 directed towards the stem. The head 31, which is slightly smaller in diameter than the bore F, is caused to pass in the hole and to protrude from the outlet U; by slightly pulling the bit backwards, moving it peripherally all around, it is possible to bevel the edge of outlet U.

To avoid damaging the underlying tissues, before inserting the tool stem 30, a flat strip 33 is inserted in the hole F. The strip 33 is folded along its entire length in a half-circle and ends with a semicircular bottom 34 adapted to keep away the tissues which must not be affected while operating with the head 31 on the other side of the edge.

The screws and holes previously used to lock the small block 9 are used for fastening the ends of the prosthetic band, which are conveniently provided with eyelets.

It has thus been observed that the invention achieves the intended aims.

The invention thus conceived is susceptible to numerous modifications and variations, all of which are within the scope of the inventive concept.

Furthermore all the details may be replaced with other technically equivalent elements.

In practice, the materials employed, as well as the shapes and dimensions, may be any according to the requirements without thereby abandoning the scope of the protection of the following claims.

We claim:

1. Apparatus for the perforation of the femur and the tibia in surgical operations, particularly for installing the front and rear crossed prosthetic ligaments in the articulation of the knee, comprising: a stem having an arc-like tapered portion, one end of said arc-like portion being adapted to be inserted in the surgical opening at the knee and pass between the tibial plate and the condyloid cavity and to be positioned in the exact outlet position of a bore to be drilled, a small block having at least one hole for a screw for fastening it to the bone, said block having a seat for engaging a spherical joint, an arm having said spherical joint at one end, said arm bearing a clamp at its end opposite said spherical joint, said clamp having a guide means, said clamp being slideable and lockable along said stem and having coupling means for interchangeable bushes for guiding a drilling tool.

2. Apparatus according to claim 1, wherein said bushes have their axis parallel to the axis of the clamp, said bushes axis having a distance from said clamp axis which is equal to the distance of the stem from the drilling tool so that the axis of the bushes is directed towards the end of the arc-like stem portion.

3. Apparatus according to claim 1, wherein said stem has a handgrip, on its side opposite to said arc-like portion.

4. Apparatus according to claim 1, wherein said bush coupling means are constituted by a counterbush which has an inclined threaded hole for a screw.

5. Apparatus according to claim 1, wherein said clamp is constituted by two jaws having respectively a groove and a countergroove articulated to one another by a pivot on one side, on the other side, a first of said jaws having an articulation for the end of a threaded stem and a second of said jaws having a fork for fastening the stem by means of a wing nut.

6. Apparatus according to claim 1, wherein a tool stem actuatable by a drill is provided for bevelling the bore outlet, said stem having a mushroom-shaped head having its abrasive side directed towards said tool stem and having a diameter which is slightly smaller than that of the bore.

7. Apparatus according to claim 6, wherein a strip is inserted in the bore before the tool stem to protect the tissues during the bevelling of the bore, said strip being curved into a half-circle, with its half-closed end adapted to protrude from the surface to be bevelled and to keep away the tissues which are not to be affected.

* * * * *